United States Patent
Shoham (10) Patent No.: US 10,687,784 B2
(45) Date of Patent: Jun. 23, 2020

(54) ULTRASOUND GUIDED HAND HELD ROBOT

(71) Applicant: MAZOR ROBOTICS LTD., Caesarea (IL)

(72) Inventor: Moshe Shoham, Hoshaya (IL)

(73) Assignee: MAZOR ROBOTICS LTD., Caesarea (IL)

( * ) Notice: Subject to any disclaimer, the term of this patent is extended or adjusted under 35 U.S.C. 154(b) by 122 days.

(21) Appl. No.: 15/307,056

(22) PCT Filed: Apr. 28, 2015

(86) PCT No.: PCT/IL2015/050436
§ 371 (c)(1),
(2) Date: Oct. 27, 2016

(87) PCT Pub. No.: WO2015/166487
PCT Pub. Date: Nov. 5, 2015

(65) Prior Publication Data
US 2017/0055940 A1  Mar. 2, 2017

Related U.S. Application Data

(60) Provisional application No. 61/996,033, filed on Apr. 28, 2014.

(51) Int. Cl.
*A61B 8/08* (2006.01)
*A61B 34/30* (2016.01)
(Continued)

(52) U.S. Cl.
CPC .......... *A61B 8/0841* (2013.01); *A61B 8/085* (2013.01); *A61B 17/3403* (2013.01);
(Continued)

(58) Field of Classification Search
CPC ..... A61B 34/30; A61B 90/11; A61B 17/3403; A61B 8/0841; A61B 8/085;
(Continued)

(56) References Cited

U.S. PATENT DOCUMENTS

| 4,669,483 A | 6/1987 | Hepp et al. |
| 6,019,724 A | 2/2000 | Gronningsaeter et al. |

(Continued)

FOREIGN PATENT DOCUMENTS

| EP | 0654244 A1 | 5/1995 |
| EP | 2147636 A1 | 1/2010 |
| WO | 2011021192 A1 | 2/2011 |

OTHER PUBLICATIONS

Pott et al.; Today's state of the art in surgical robotics; Computer Aided Surgery; Mar. 2005; 10(2); pp. 101-132; publication date Mar. 2005 (Year: 2005).*

(Continued)

*Primary Examiner* — Amanda Lauritzen Moher
*Assistant Examiner* — Chao Sheng
(74) *Attorney, Agent, or Firm* — Sheridan Ross P.C.

(57) ABSTRACT

A system for insertion of a surgical tool along a trajectory to a target region in a patient's tissues, under the guidance of ultrasound imaging. The system includes a hand-held robot to whose base the probe of an ultrasound system is rigidly connected. The activated platform of the hand held robot carries a surgical tool guide. The alignment of the tool guide defines the trajectory which the tool takes within the subject's body. The position of the target region seen on the ultrasound display, can be recorded, and the robot coordinate frame of reference registered thereto. The system aligns the pose of the robot such that the surgical tool is aimed directly at the target region, independently of motion of the ultrasound probe and its associated robot. An inertial measure- (Continued)

ment unit can be incorporated to provide back-up positional information if the image of the lesion is lost.

15 Claims, 3 Drawing Sheets

(51) Int. Cl.
*A61B 90/11* (2016.01)
*A61B 17/34* (2006.01)
*A61B 34/20* (2016.01)
*A61B 90/00* (2016.01)
*A61B 18/14* (2006.01)

(52) U.S. Cl.
CPC .............. *A61B 34/30* (2016.02); *A61B 90/11* (2016.02); *A61B 2017/3413* (2013.01); *A61B 2018/1425* (2013.01); *A61B 2034/2048* (2016.02); *A61B 2034/2065* (2016.02); *A61B 2034/304* (2016.02); *A61B 2090/378* (2016.02)

(58) Field of Classification Search
CPC .... A61B 2034/2048; A61B 2034/2065; A61B 2034/304; A61B 2090/378; A61B 2017/3413; A61B 2018/1425
See application file for complete search history.

(56) References Cited

U.S. PATENT DOCUMENTS

| | | | |
|---|---|---|---|
| 6,216,029 B1* | 4/2001 | Paltieli | A61B 8/0833 600/411 |
| 6,875,179 B2* | 4/2005 | Ferguson | A61B 8/0833 600/461 |
| 2002/0156376 A1* | 10/2002 | Wang | A61B 8/0833 600/439 |
| 2003/0233046 A1 | 12/2003 | Ferguson et al. | |
| 2005/0154302 A1 | 7/2005 | Sela et al. | |
| 2006/0106306 A1 | 5/2006 | Essner et al. | |
| 2012/0265071 A1* | 10/2012 | Berke | A61B 1/00149 600/439 |
| 2012/0277585 A1 | 11/2012 | Koenig et al. | |
| 2014/0343406 A1* | 11/2014 | Damjanovic | A61B 8/0841 600/424 |

OTHER PUBLICATIONS

Grey Lerner; Dissertation: A Passive Seven Degree of Freedom Positioning Device for Surgical Robots and Devices; Johns Hopkins University; 1998 (Year: 1998).*
International Search Report and Written Opinion of the ISA, in PCT/IL2015/050436, dated Aug. 18, 2015.
European Supplementary Search Report and Written Opinion in EP 15785365.6-1659, dated Nov. 23, 2017, corresponding to the present Application.

* cited by examiner

ULTRASOUND GUIDED HAND HELD ROBOT

This is a 35 U.S.C. § 371 application of PCT/IL2015/050436, filed Apr. 28, 2015, and claims the benefit under 35 U.S.C. § 120 of said PCT application, and further claims the benefit under 35 U.S.C. § 119(e) of U.S. Provisional Patent Application Ser. No. 61/996,033, filed Apr. 28, 2014. The contents of these priority applications are incorporated herein by reference.

FIELD OF THE INVENTION

The present invention relates to the field of the use of ultrasound imaging of a surgical site, especially for the robotic delineation of an access trajectory to a region of interest within a subject's tissue, imaged using an ultrasound system.

BACKGROUND OF THE INVENTION

Needle insertion to access a target region in a subject's tissues, such as a lesion, for instance, is a common clinical procedure, carried out in order to perform procedures such as a tissue biopsy, or to perform a minor surgical procedure, or for the insertion of a diagnostic or therapeutic probe. Currently, guidance of a surgical needle insertion into a tissue to a target lesion can be performed manually under ultrasound (US) guidance, by observation of the lesion in the ultrasound image and by estimation of the correct insertion point and angle to be used in order to access the lesion with the needle. The accuracy of this procedure is highly dependent upon the skill of the doctor performing the procedure. Computer assisted guided insertion can also be performed using ultrasound imaging, by using a navigation system in order to track both the position of the ultrasound probe, and the position of the tool guide or the tool itself. The navigation system can then ensure that when the ultrasound probe is held at such an angle that the target lesion falls in a predefined position on the screen, the tool guide or the tool can be directed, either manually or by a robot to pass through the position of the lesion. Use of a virtual trajectory of the tool path, or a virtual image of the tip of the needle, projected onto the ultrasound image, can make this procedure accurate and simple for the doctor to execute. However, this system requires a navigation system which tracks and correlates between two distinct bodies, and the system is therefore generally complex and costly.

There therefore exists a need for a ultrasound guidance system, which enables access to a target point within the subject's tissue, and which overcomes at least some of the disadvantages of prior art systems and methods.

The disclosures of each of the publications mentioned in this section and in other sections of the specification, are hereby incorporated by reference, each in its entirety.

SUMMARY

The present disclosure describes new exemplary systems and methods for performing insertion of a surgical tool along a trajectory to a target region in a patient's tissues, under the guidance of ultrasound imaging. The systems are based on a hand-held robot to whose base the probe of an ultrasound system is rigidly connected. The activated platform of the hand-held robot may carry a tool guide, through which the surgical tool is passed. The alignment of the tool guide defines the trajectory which the tool will take on entering the subject's body. Such a hand held robot has been described in PCT International Patent Application published as WO 2011/021192 for "Device for Improving the Accuracy of Manual Operations" having common inventorship with the present application, and incorporated by reference herein, in its entirety. The robot of the present application differs in that it has an ultrasound probe firmly attached to its base, and that it does not need any separate navigation system sensors to define its position in space. The doctor scans the region of interest with the ultrasound probe, until the target region is seen on the display screen. The target region may typically be a lesion or another tissue sample which it is desired to access or treat with the surgical tool, and while a lesion is used an example in the present application, it is to be understood that any other physiological feature could also be the target to be treated. When the doctor has found the target lesion by manipulation of the ultrasound probe, its position can be marked on the screen, such as by use of a mouse-click, and the ultrasound imaging software is adapted to record the registered position of the lesion in the ultrasound image frame of reference for that particular position of the ultrasound probe. The position of the lesion is thus now known relative to the position of the ultrasound probe, and since the ultrasound probe is rigidly attached to the base of the robot, the position of the lesion is thus now also known relative to the co-ordinate frame of reference of the hand-held robot, and hence of the tool guide. The system can now align the pose of the hand held robot such that the tool guide is aimed directly at the target lesion, and a surgical tool passed through the tool guide and into the subject's tissues, will impinge on the target lesion. As the surgeon moves his hand while holding the robot and scanning the region of interest, the system applies a correction feedback signal to the robot control, and the robot will adjust its pose so that the tool guide will maintain the tool in the same trajectory relative to the imaged lesion, and is thus always directed at the lesion regardless of the position of the probe.

The system operation depends upon the provision of the correct feedback between the position of the lesion marked on the screen, and the real-life position of the lesion as targeted by the tool guide. The currently described system can achieve this by two methods. One method is by using image processing techniques on the position of the lesion in the image on the screen. As the position of the lesion on the US image changes with change in the position and orientation of the US probe, the system analyses the motion of that position and provides an appropriate feedback signal to the robot in order to adjust the pose of the tool guide to compensate for the motion of the robot base, and thus to keep the tool guide directed at the lesion in real life. This is the preferred feedback method, since it depends on direct identification of the position of the lesion in the ultrasound image generated by the doctor. However, a number of problems can arise when using this method. Firstly, if the doctor were to make a sudden movement of the ultrasound probe, or if the image quality were to degrade temporarily due to any cause, this may cause the tracking software to lose its tracked position of the lesion. Furthermore, if the doctor were to raise the robot such that the ultrasound probe no longer makes contact with the subject's skin, the ultrasound image of the lesion gets lost, and when contact is again made with the subject's skin, there is no guarantee that the lesion will be picked up again within the image obtained. Therefore, this image processing method may generally be operable only under conditions in which the lesion is maintained within the field of view on the ultrasound image.

In order to circumvent the above described problems arising from loss of the position of the lesion in the ultrasound image, an alternative system based on an inertial measurement unit (IMU) can be used. The IMU is mounted in or on the robot in order to keep track of the position of the robot in space. In this system, the position of the tool guide relative to the initial image of the lesion on the screen is registered as the base reference position of the IMU. As the surgeon changes the position of his hand, and the robot and its associated ultrasound probe move, the IMU continually measures the acceleration and the orientation of the body of the robot, and can thus provide feedback to the robot control about the absolute position in space of the robot. The robot control can then use this absolute position data to adjust the pose of the robot in order to keep the tool guide directed at its original position, aimed at the target lesion, regardless of the change in position and orientation of the robot body. Once the IMU unit has locked onto the position of the image of the lesion, there is no longer any need for the lesion to be visible in the image on the screen. The position of the robot body is entirely defined by the output signals of the IMU. The IMU can be MEMS implemented, such that the size of the IMU can be made sufficiently small that it can be installed on the circuit board of the hand held robot.

However, there is a problem in the sole use of an IMU to track the robot position in space, arising from the drift which is inherent in such IMU devices. The extent of this drift naturally depends on the quality level of the IMU used, and hence its cost. Furthermore, as indicated above, the preferred system of tracking is that based on image processing to follow the actual position of the target on the US image, but this can be limited by loss of the US image when the US probe is lifted from the subject's skin. Therefore, in order to overcome this problem of the loss of the lesion position, it is possible to improve the overall ability of the system to accurately track the position of the lesion in the robot frame of reference by combining the two tracking systems, namely, tracking the lesion on the US image by image processing and reversion to the IMU to follow the robot position in case of complete loss of US image by separation of the US probe from the skin, or in the case of the image processing algorithm itself losing track of the lesion motion. The IMU maintains the robot in the region of the lesion while no positive image location is possible, but once good image processing of the lesion position again becomes possible, accurate positioning is again made by the image processing tracking algorithm.

The ultrasound guidance system of the present disclosure differs from prior art imaging and robotic guidance systems, in that the robot base is physically attached to the imaging system reference frame. As a result, no registration procedure using an intermediate object is required in order to correlate the coordinate system of the images generated, with the coordinate system of the robot, and hence of the surgical tool guided by the robot. This effectively means that the image of the lesion itself behaves virtually as if it were connected to the base of the robot, thereby maintaining accurate registration between the robot coordinates and the real life position of the lesion itself. Furthermore, the system of the present disclosure eliminates the need for a separate tracking system or dynamic referencing fiducials attached firmly to the patient.

There is thus provided in accordance with an exemplary implementation of the system described in this disclosure, a system comprising:

(i) a hand held robot comprising a base and an actuated arm, (ii) an ultrasound imaging probe attached to the base of the hand held robot, such that when the robot is moved, the ultrasound imaging probe moves with it, and such that the co-ordinate system of the field of view of the ultrasound imaging probe is co-registered to the co-ordinate system of the robot, (iii) a tool guide attached to the actuated arm of the hand held robot, and (iv) a control system adapted to utilize the co-registration of the co-ordinate systems of the ultrasound imaging probe and the robot to adjust the pose of the robot actuated arm, such that as the ultrasound imaging probe is moved, the position and orientation of the tool guide is adjusted by the control system in order to maintain its direction relative to a feature imaged by the ultrasound imaging probe.

In such a system, the control system may utilize image processing of a real time ultrasound image of the feature in order to adjust the pose of the actuated arm to maintain its direction relative to the feature.

Additionally, the control system may define the position of the feature in the co-ordinate system of the field of view of the ultrasound probe, and may be adapted to utilize the co-registration between the frame of reference of the ultrasound imaging probe and the robot co-ordinate system in order to adjust the robot arm to maintain its pose directed at the feature imaged using the ultrasound imaging probe.

In any of the above described systems, the hand-held robot may further comprise an inertial measurement unit adapted to track the absolute pose of the robot in space, and to provide an output to the control system to enable maintenance of the trajectory of the actuated arm in space with change in the position and orientation of the hand held robot. Alternatively, the hand-held robot may further comprise an inertial measurement unit adapted to provide an output to the control system which tracks the absolute pose of the robot in space, and wherein the control system utilizes the output to enable maintenance of the trajectory of the actuated arm in space when the image processing is unable to determine the feature in the real time ultrasound.

In any of the above described systems, the feature may be a lesion in the tissue of a subject. Additionally, the tool guide may be adapted to accommodate a surgical tool, which furthermore may be any one of a hypodermic needle, a biopsy needle, a drug delivery needle, an ablation electrode, a brachytherapy applicator, or an electrode positioning device.

Yet another implementation described in this disclosure performs a method of targeting a feature in the body of a subject, comprising:

(i) providing a hand-held robot having a base and an actuated arm, and having a probe of an ultrasound system attached to the base, such that the position of an object imaged in the ultrasound system is defined relative to the co-ordinate system of the robot, (ii) identifying the feature in an image generated using the ultrasound system, (iii) using the identified position of the feature in the ultrasound image to register the position of the feature in the coordinate system of the robot, and (iv) aligning the robot such that a tool held in a guide tube attached to the actuating arm is directed at the feature.

Such a method may further comprise the steps of:

(v) tracking the position of the feature in the ultrasound image as the ultrasound probe is moved across the body of the subject, and (vi) generating a feedback control signal for the hand held robot according to any tracked motion of the feature, so as to adjust the pose of the robot arm such that the tool remains directed at the feature despite motion of the ultrasound probe.

Furthermore, in any of the above-described methods, the hand-held robot may further comprise an inertial measurement unit adapted to track the absolute orientation of the robot in space, and to provide an output to enable maintenance of the pose of the actuated arm in space with change in the position and orientation of the hand-held robot. Alternatively, the hand-held robot further comprises an inertial measurement unit adapted to track the absolute orientation of the robot in space, and to provide an output to enable maintenance of the pose of the actuated arm in space with change in the position and orientation of the hand-held robot, and wherein the method utilizes the output to maintain the trajectory of the actuated arm in space when the position of the feature cannot be tracked in the ultrasound image as the ultrasound probe is moved across the body of the subject.

BRIEF DESCRIPTION OF THE DRAWINGS

The present invention will be understood and appreciated more fully from the following detailed description, taken in conjunction with the drawings in which.

DETAILED DESCRIPTION

Figure 1:
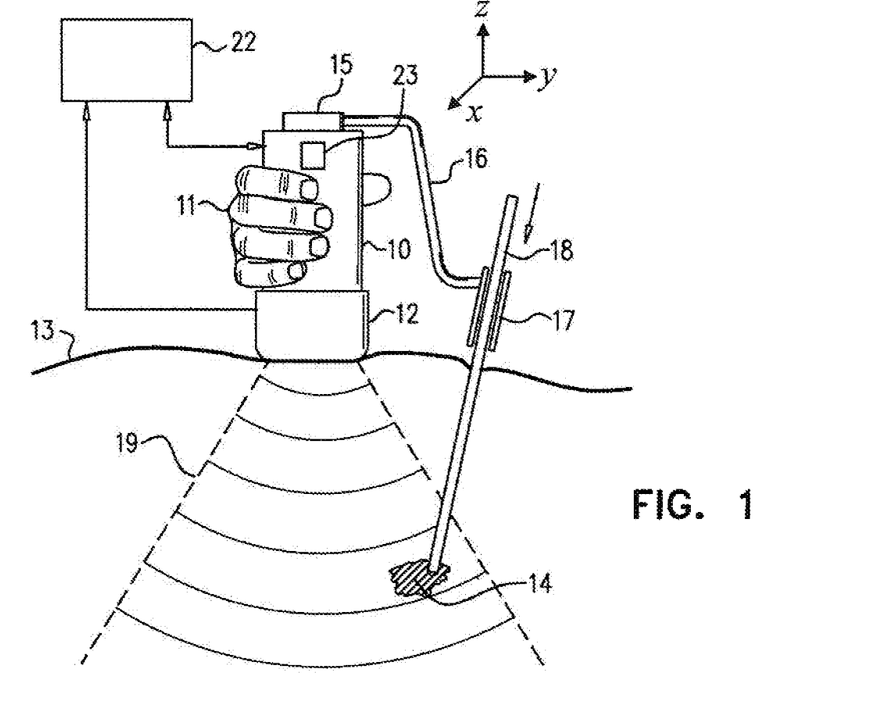
FIG. 1 shows an exemplary ultrasound guided hand held robotic system of the type described in this disclosure.

Reference is now made to FIG. 1, which illustrates schematically an exemplary ultrasound-guided hand held robotic system of the type described in this disclosure. The body of the robot 10 can be comfortably gripped by the doctor 11 during the procedure. An ultrasound probe 12 is firmly attached to the base of the robot, so that the doctor can scan the skin 13 of the patient with the ultrasound probe, to generate an ultrasound image of the patient's anatomy. In FIG. 1, the ultrasound scan 19 is shown having detected a lesion 14 in the patient's tissue. To the actuated platform 15 of the robot 10, there is attached an arm 16, to the end of which a surgical guide or sleeve 17, is attached. A surgical tool, such as the needle 18, can be directed through this tool guide 17, such that when the robot is correctly aligned, the needle will reach the lesion 14. In FIG. 1, the needle is shown for manual insertion, but it is to be understood that a controlled micro-drive (not shown) can alternatively be mounted on the tool guide to control the entry of the needle 18. The ultrasound-guided hand held robotic system further comprises a control system 22 which receives information from the ultrasound system display data, and outputs and inputs information to and from the robot actuators and encoders, and from any inertial measurement unit 23 mounted in or on the robot or on the arm 16. The control system 22 could be one integrated unit for all of the functions required by the system, or it could have separate modules for ultrasound generation and/or imaging functions, for trajectory pose calculation by ultrasound image processing or from the IMU, and for robot control.

Figure 2:
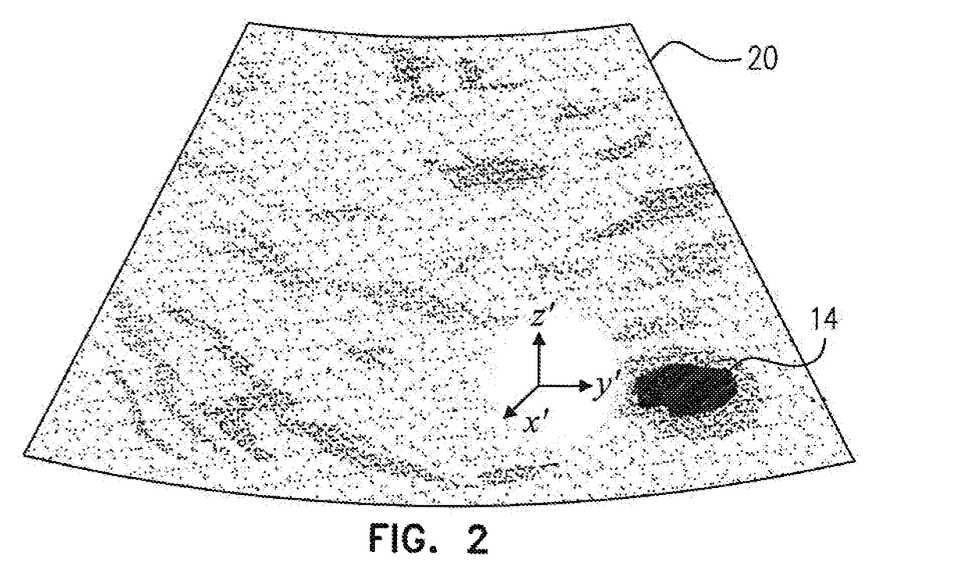
FIG. 2 shows a view of the imaging screen of the ultrasound system, showing a target lesion displayed in the image.

Reference is now made to FIG. 2, which illustrates schematically a view of an ultrasound image 20 obtained using the ultrasound probe 12 of FIG. 1, with the lesion 14 shown in the bottom right-hand corner of the image.

Figure 3:
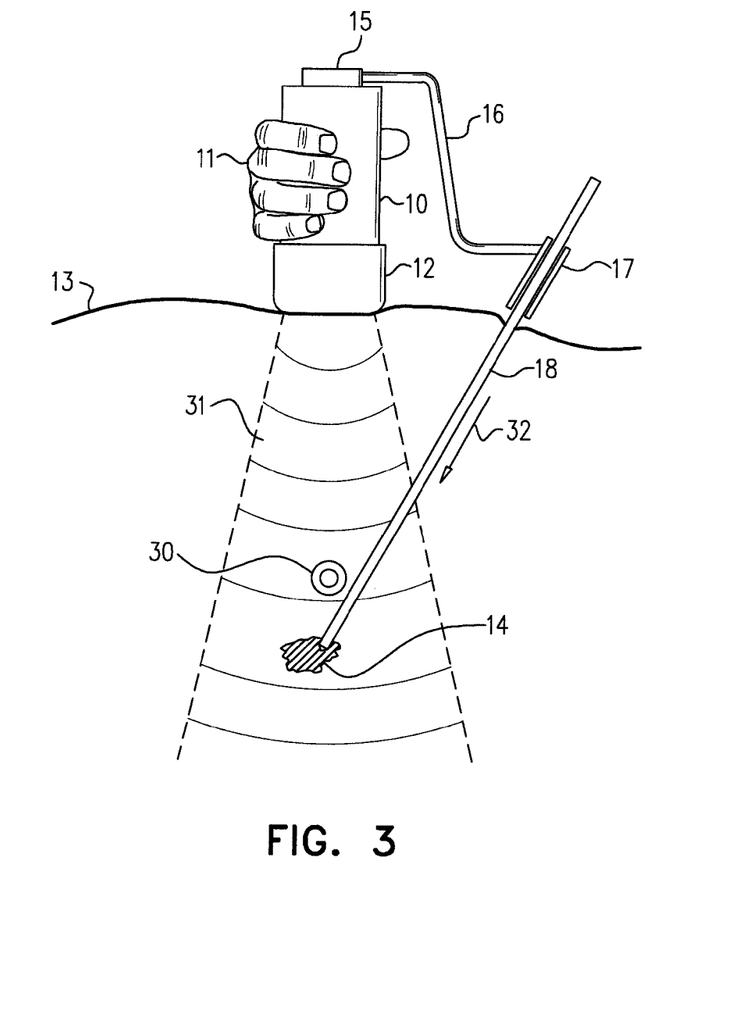
FIG. 3 is a view of the region of interest shown in FIG. 1, taken from the direction within the plane of the drawing of FIG. 1.

Reference is now made to FIG. 3, which illustrates one of the advantages of using the hand held robot 10 of FIG. 1. FIG. 3 is a view of the system and region of interest shown in FIG. 1, taken from the direction within the plane of the drawing of FIG. 1. Unlike other imaging methods, an ultrasound scan can only view a limited imaged field, approximating a two-dimensional plane, as shown by the limited borders of the scanned field of view 31 in the plane shown. Usually the limits of the imaged view have a limited cone angle, which can sometimes be up to about 30 degrees. That approximately two-dimensional plane should include the lesion 14 to be treated, or different slices thereof. Therefore, the complete access path of the surgical tool 18 to the lesion 14 to be treated, can only be observed using the ultrasound scan, if that access path falls within the approximately two-dimensional plane 31 of the ultrasound scan. However, that plane may include features such as a bone, or a vital blood vessel 30 or organ or nerves, through which it is impossible or dangerous to perform a surgical insertion. By using the hand held robot system of the present application, it becomes possible to keep the lesion 14 within view in the approximately two-dimensional plane of view 31 of the ultrasound scan, and at the same time to provide access to the lesion 14 by inserting the surgical tool 18 from a direction 32 other than that within the plane of view 31 of the ultrasound image, so that the surgical tool does not have to pass through the region with the obstruction. The accuracy of the target position of the lesion 14 as determined in the ultrasound image is thus maintained, but without the need to pass through forbidden regions 30 in the plane of the ultrasound image in order to insert the surgical tool to the lesion since there is no need now to maintain the lesion and the surgical tool in the same ultrasound sensing plane.

Figure 4:
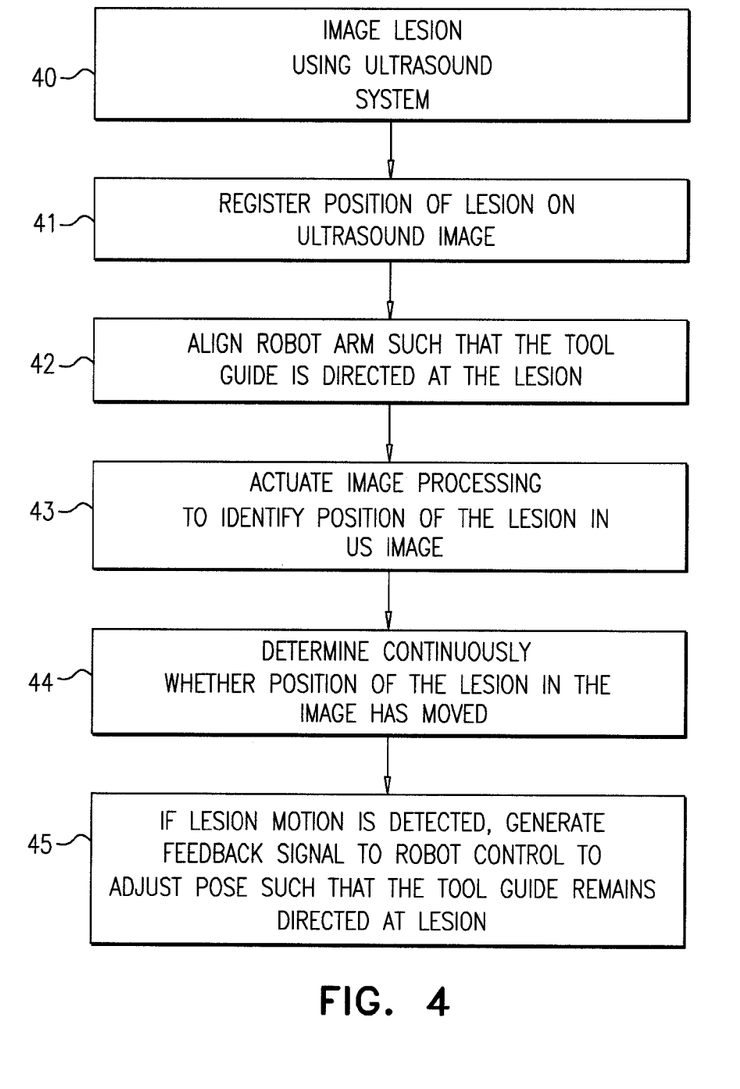
FIG. 4 is a flowchart showing the way in which the system operates to maintain the tool guide directed at a target area as the ultrasound probe is moved.

Reference is now made to FIG. 4, which is an exemplary flowchart showing one way in which the system operates to maintain the tool guide directed at a target area as the ultrasound probe is moved. In step 40, the ultrasound probe scans the region of interest until the position of a lesion has been detected in the US image. In step 41, the user causes the recording of the position of the lesion on the US image. In step 42, based on that recorded position, the control system moves the robot pose such that the tool guide is directed in real life at the lesion. In step 43, an image processing software routine is actuated on the US image, to lock onto the position of the lesion in that image. In step 44, as the position of the robot with its attached ultrasound probe is moved, the image processing software tracks the position of the moving lesion image. In step 45, the control system uses the tracked position of the moving lesion image to generate a correction signal for the robot control to adjust the robot pose such that the tool guide remains directed at the lesion as the robot base moves.

If an inertial measurement unit is used to control the robot pose, then only steps 40 to 42 need to be performed in the above described method, and at step 43, the IMU is actuated to lock that position of the tool guide as the reference position to be maintained as the robot body moves by means of a feedback signal from the IMU to the robot control system.

If a combination of the image processing and IMU is used to control the robot pose, then after step 42, the IMU is actuated to register the pose of the robot relative to the detected position of the lesion in the US image, but the guidance of the robot is continued through steps 43 to 45 using signal processing of the lesion position in the US images. The IMU determined pose of the robot is continued to be recorded in the background, so that should the image processing lose track of the lesion at any stage during step 45, then at that point, an additional step is required after step 45, in which the IMU feedback is used to take over from the image processing feedback, and to continue to update the inertial location of the robot relative to the lesion, until a sufficiently good image of the lesion is obtained to enable reactivation of the image processing tracking procedure.

Use of the present ultrasound guided hand held robot has an added advantage in that the insertion trajectory is determined ab initio, before commencement of the insertion, such that the needle is always accurately directed to the target lesion. Since it is difficult to change the insertion trajectory of a needle once it is within the subject's tissue, this system therefore assists in preventing the need to change the needle trajectory once insertion has begun.

Furthermore, while the insertion is being implemented, the surgeon can freely continue to perform ultrasound scans around the region of interest, by continuously moving the position or angle of the US probe to identify the treated area better and more accurately, and to observe the progress of the insertion or the position of the lesion or the location of other objects near the lesion, without affecting the accuracy of insertion of the needle despite the motion of the robot base.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

I claim:

1. A system comprising:
    a hand-held robot comprising a base and an actuated arm;
    an ultrasound imaging probe attached to the base of the hand-held robot, wherein a co-ordinate system of a field of view of the ultrasound imaging probe is co-registered to a co-ordinate system of the robot;
    a tool guide attached to the actuated arm of the hand-held robot; and
    a control unit configured to use information received from the ultrasound imaging probe to provide a feedback signal to a automatically adjust a pose of the actuated arm as the ultrasound imaging probe is moved, thus automatically maintaining a direction of the tool guide relative to a feature imaged by the ultrasound imaging probe.

2. The system of claim 1, wherein the control unit is configured to automatically adjust the pose of the actuated arm, thus automatically maintaining the direction of the tool guide relative to the feature, by utilizing image processing of real time ultrasound images of the feature.

3. The system of claim 1, wherein the control unit is configured to define a position of the feature in the co-ordinate system of the field of view of the ultrasound imaging probe and to automatically adjust the pose of the actuated arm to maintain the pose directed at the position.

4. The system of claim 1, wherein the hand-held robot further comprises an inertial measurement unit adapted to track an absolute pose of the robot in space, and to provide an output to enable automatic maintenance of the pose of the actuated arm in space with change in a position and orientation of the hand-held robot.

5. The system of claim 1, wherein the hand-held robot further comprises an inertial measurement unit adapted to provide an output which tracks an absolute pose of the robot in space, and wherein the control unit utilizes the output to enable automatic maintenance of the pose of the actuated arm in space when the image processing is unable to determine a position of the feature in the real time ultrasound image.

6. The system of claim 1, wherein the feature is a lesion in a tissue of a subject.

7. The system of claim 1, wherein the hand-held robot automatically maintains the direction of the tool guide relative to the feature imaged by the ultrasound imaging probe even in a plane different from that of the field of view of the ultrasound imaging probe.

8. The system of claim 1, wherein the tool guide is adapted to accommodate a surgical tool.

9. The system of claim 8, wherein the surgical tool is a hypodermic needle, a biopsy needle, a drug delivery needle, an ablation electrode, a brachytherapy applicator, or an electrode positioning device.

10. A method of targeting a feature in a body of a subject, comprising:
    using an ultrasound probe to identify, in an ultrasound image, a feature in a body of a subject, the ultrasound probe being attached to a base of a hand-held robot having an actuated arm whose pose is defined in a coordinate system of the hand-held robot, such that the feature imaged by the ultrasound probe has a position defined relative to the co-ordinate system of the hand-held robot by virtue of the attachment of the ultrasound probe to the base of the hand-held robot;
    aligning the hand-held robot such that a tool held in a guide tube attached to the actuated arm is directed at the feature;
    tracking the position of the feature in the ultrasound image as the ultrasound probe is moved across the body of said subject;
    generating a feedback control signal for the hand-held robot according to the tracked position of the feature in the ultrasound image; and
    using the feedback control signal to automatically adjust the pose of the actuated arm, such that the tool remains directed at the feature despite motion of the ultrasound probe.

11. The method of claim 10, wherein the feature is a lesion in the tissue of the subject.

12. The method of claim 10, wherein the hand-held robot further comprises an inertial measurement unit that tracks an orientation of the hand-held robot in space, and provides an output to enable maintenance of the pose of the actuated arm in space with a change in a position and orientation of the hand-held robot.

13. The method of claim 12, further comprising:
    utilizing the output to maintain the pose of the actuated arm in space at times when the position of the feature cannot be tracked in the ultrasound image as the ultrasound probe is moved across the body of the subject.

14. The method of claim 10, wherein the tool held in the guide tube is a surgical tool.

15. The method according to claim 14, wherein the surgical tool is a hypodermic needle, a biopsy needle, a drug delivery needle, an ablation electrode, a brachytherapy applicator, or an electrode positioning device.

\* \* \* \* \*

UNITED STATES PATENT AND TRADEMARK OFFICE
CERTIFICATE OF CORRECTION

PATENT NO. : 10,687,784 B2
APPLICATION NO. : 15/307056
DATED : June 23, 2020
INVENTOR(S) : Moshe Shoham

Page 1 of 1

It is certified that error appears in the above-identified patent and that said Letters Patent is hereby corrected as shown below:

In the Claims

Claim 1, Column 7, Line 49, delete "signal to a automatically adjust a pose of the actuated", and insert --signal to automatically adjust a pose of the actuated--

Signed and Sealed this
First Day of September, 2020

Andrei Iancu
*Director of the United States Patent and Trademark Office*